(12) United States Patent
Grundei

(10) Patent No.: US 6,358,222 B1
(45) Date of Patent: Mar. 19, 2002

(54) SHUNT VALVE

(75) Inventor: Hans Grundei, Lübeck (DE)

(73) Assignee: Adeva Medical GmbH & Co., Lübeck (DE)

( * ) Notice: Subject to any disclaimer, the term of this patent is extended or adjusted under 35 U.S.C. 154(b) by 0 days.

(21) Appl. No.: 09/333,280

(22) Filed: Jun. 15, 1999

Related U.S. Application Data

(63) Continuation of application No. PCT/EP97/06852, filed on Dec. 9, 1997, now abandoned.

(30) Foreign Application Priority Data

Dec. 16, 1996 (DE) .......................... 196 51 951

(51) Int. Cl.⁷ .............................. A61M 5/00; A61F 2/20
(52) U.S. Cl. ................................... 604/9; 604/8; 623/9
(58) Field of Search ........ 604/8–9; 128/200.24–200.26, 128/202.29, 203.11, 207.14, 207.15, 207.16; 623/9

(56) References Cited

U.S. PATENT DOCUMENTS

| 4,040,428 A | * | 8/1977 | Clifford ...................... 128/351 |
| 4,044,402 A | * | 8/1977 | Edwards ..................... 128/351 |
| 4,582,058 A | * | 4/1986 | Depel et al. ........... 128/207.17 |
| 4,614,516 A | * | 9/1986 | Blom et al. ..................... 623/9 |
| 4,820,304 A | | 4/1989 | Depel et al. |
| 4,911,716 A | * | 3/1990 | Blom et al. ..................... 623/9 |
| 5,107,828 A | * | 4/1992 | Koss et al. ............. 128/200.26 |
| 5,123,922 A | * | 6/1992 | Berg ............................ 623/9 |
| 5,391,205 A | * | 2/1995 | Knight .......................... 623/9 |
| 5,578,083 A | * | 11/1996 | Laguette et al. ................ 623/9 |
| 5,738,095 A | * | 4/1998 | Persson ................. 128/207.14 |
| 5,746,725 A | * | 5/1998 | Shalon et al. ............... 604/246 |
| 5,881,718 A | * | 3/1999 | Mortensen et al. ..... 128/203.11 |

FOREIGN PATENT DOCUMENTS

| DD | 275 183 A1 | 1/1990 |
| DE | 32 11 126 A1 | 11/1982 |
| EP | 0 222 509 A2 | 5/1987 |
| EP | 0 299 705 A2 | 1/1989 |
| EP | 0 651 980 A2 | 5/1995 |
| FR | 2 494 581 | 5/1982 |
| WO | WO96/14031 A1 | 5/1996 |
| WO | WO 97/45075 | 12/1997 |

* cited by examiner

Primary Examiner—Angela D. Sykes
Assistant Examiner—Patricia Bianco
(74) Attorney, Agent, or Firm—Akin, Gump, Strauss, Hauer & Feld, L.L.P.

(57) ABSTRACT

A shunt valve is provided for insertion into a surgically produced connecting canal between the trachea and the esophagus. The valve has a tube-like section (1) with an open lumen (11) to be turned towards the trachea and a closable lumen end (14) which is to be turned towards the esophagus and which can be closed by a flap valve (2) functioning on one side. The flap (3) of the valve is spring loaded in such a way that the flap valve (2) remains in closed position during insufficient counterforce and allows a flow of air from the trachea to the esophagus during inhalation and opening of the flap (3). The tubular section (1) is provided with a physiologically compatible plastic sleeve (4). The pivoting area (7) of the flap (3) of the flap valve (2) is substantially completely covered by a roof-like protuberance (10) of the plastic sleeve. An elastic force acting upon the flap (3) is produced by a restoring spring (8) formed in the roof-like covering area of the plastic sleeve (4) and coming into direct contact with the flap (3) at one of its ends (9), thereby forcing the flap into the closed position.

4 Claims, 1 Drawing Sheet

SHUNT VALVE

CROSS REFERENCE TO RELATED APPLICATION

This application is a continuation of International Application PCT/EP97/06852, filed Dec. 9, 1997, now abandoned, the disclosure of which is incorporated herein by reference.

BACKGROUND OF THE INVENTION

The present invention relates to a so-called shunt valve, which is applied in a known manner after a laryngectomy performed on a patient, in a surgically produced connection channel between the trachea and esophagus, which is the so-called shunt. This makes it possible for the patient to carry out, along with the air conductance that is necessary for life, also an air conductance for generating sound, i.e. for speech, through a surgically created tracheostomy. If the patient closes the tracheostomy by hand while exhaling, or if the tracheostomy is closed by a tracheostomy valve when a predetermined pressure is exceeded, air can pass out of the trachea into the esophagus, through an artificially produced connection channel, and can be used for the formation of sounds.

Shunt valves function primarily for the purpose of keeping open the artificial connection channel. In addition to that, however, they have an another important function of not allowing secretions and food particles to pass from the esophagus into the trachea, which would otherwise cause severe complications. For this purpose, valves operating on one side have been proposed on the esophagus end of the shunt valve, for example in German published patent application DD-A-275 183 in the form of a flap valve or according to DE-A-32 11 126 in the formation of a tube that is itself closed on the esophagus end, which only provides a valve slit through which air can be conducted from the trachea into the esophagus as desired.

The solutions proposed thus far have, however, only a sub-optimal sealing effect and are hardly convincing in practice. Thus, it is constantly recurring in the known shunt valves that food particles or secretions pass into the trachea, which can cause severe difficulties for the patient.

A voice prosthesis of the generic type according to the construction of French published patent application according to FR 2494581. A also does not create a remedy to improve this situation. This publication shows a voice prosthesis to be applied in a surgically produced connection channel between the trachea and esophagus, which has a tube-shaped part having an open lumen to be turned toward the trachea and a closable lumen to be turned toward the esophagus, which can be closed through a flap valve acting on one end, the flap of which stays in its closed position when there are no opposing forces, and which upon inhalation, in opening the flap, allows an air flow from the trachea into the esophagus. On the esophagus end, the possibility is not to be ruled out that food particles can enter into the tube-shaped part and thus stop up the lumen of the shunt valve or even pass into the trachea, where they can cause severe coughing fits or cases of suffocation.

From U.S. Pat. No. 4,820,304, another voice prosthesis is known in which it is proposed to form on the shunt valve on the esophagus end, a roof-like cover, and which acts against an entry of food particles into the inside of the valve.

SUMMARY OF THE INVENTION

In view of this background, an object of the invention presented here is to create a remedy for this situation, i.e. to provide a shunt-valve that shows a decisive improvement compared to the known solutions in regard to sealing function of the trachea from the esophagus. This purpose is achieved through a shunt valve according to the present invention, for which advantageous embodiments are described below.

Accordingly, as an improvement of the shunt valve according to the generic concept described above, it is proposed that (1) the tube-shaped part is provided with a plastic sheath that is physiologically compatible, (2) the pivot area of the flap of the flap valve is substantially completely covered by a roof-like protuberance of the plastic sheath, and (3) an elastic force acting on the flap is produced by a restoring spring that contacts the flap directly at one end, the restoring spring being formed on the roof-like protuberance of the plastic sheath, and urges the flap into the closed position.

The realization of the first feature above in regards to the tube-shaped part leads to the actual core piece of the shunt valve, namely the tube-shaped part, forming more or less a reinforcement for the plastic sheath, which can be made of silicone, for example. The physiological compatibility is thus clearly improved by this. In addition, the inner tube piece can be pulled out of the plastic sheath for cleaning purposes, while the plastic sheath can remain in place.

The second and third features above lead to a clear increase of the safety of the shunt valve according to the invention. The solution of the formed (molded-on) restoring spring is, moreover, especially cost-effective to manufacture, since the restoring spring can form a single-piece component of the remaining plastic sheath.

The active closing of the flap valve through the restoring forces of the restoring spring acting on the flap of the valve offers a considerably higher safety than the passively acting valve members of the known shunt valves, so that the traditional complications do not have to be reckoned with in wearing the shunt valve according to the invention.

The installation position of the shunt valve should be such that the flap opens in the caudal direction, whereas the roof-like protuberance forms a quasi-shield in the cranial direction.

Preferably, the inner tube-shaped part is made of a physiologically compatible metal. This offers the possibility of a sufficient mechanical stability, where the flap of the flap valve on the esophagus end can also be made of metal and have a truncated cone shape, in order to obtain an optimal sealing.

The stability of the position of the shunt valve in the connection channel between the trachea and esophagus can be advantageously increased by forming on the plastic sheath two surrounding flanges, between which the esophagus wall and the trachea wall come to rest. These walls are surgically connected together in the area of the connection channel, for example sewn together, so that both walls lie together between the flanges.

BRIEF DESCRIPTION OF THE DRAWING

The foregoing summary, as well as the following detailed description of the invention, will be better understood when read in connection with the appended drawings. For the purpose of illustrating the invention, there are shown in the drawings embodiment(s) which are presently preferred. It should be understood, however, that the invention is not limited to the precise arrangements and instrumentalities shown. In the drawings:

The sole FIGURE of the drawing is a longitudinal cross-sectional view of a shunt valve according to a preferred embodiment of the invention.

DETAILED DESCRIPTION OF THE INVENTION

Figure 1:
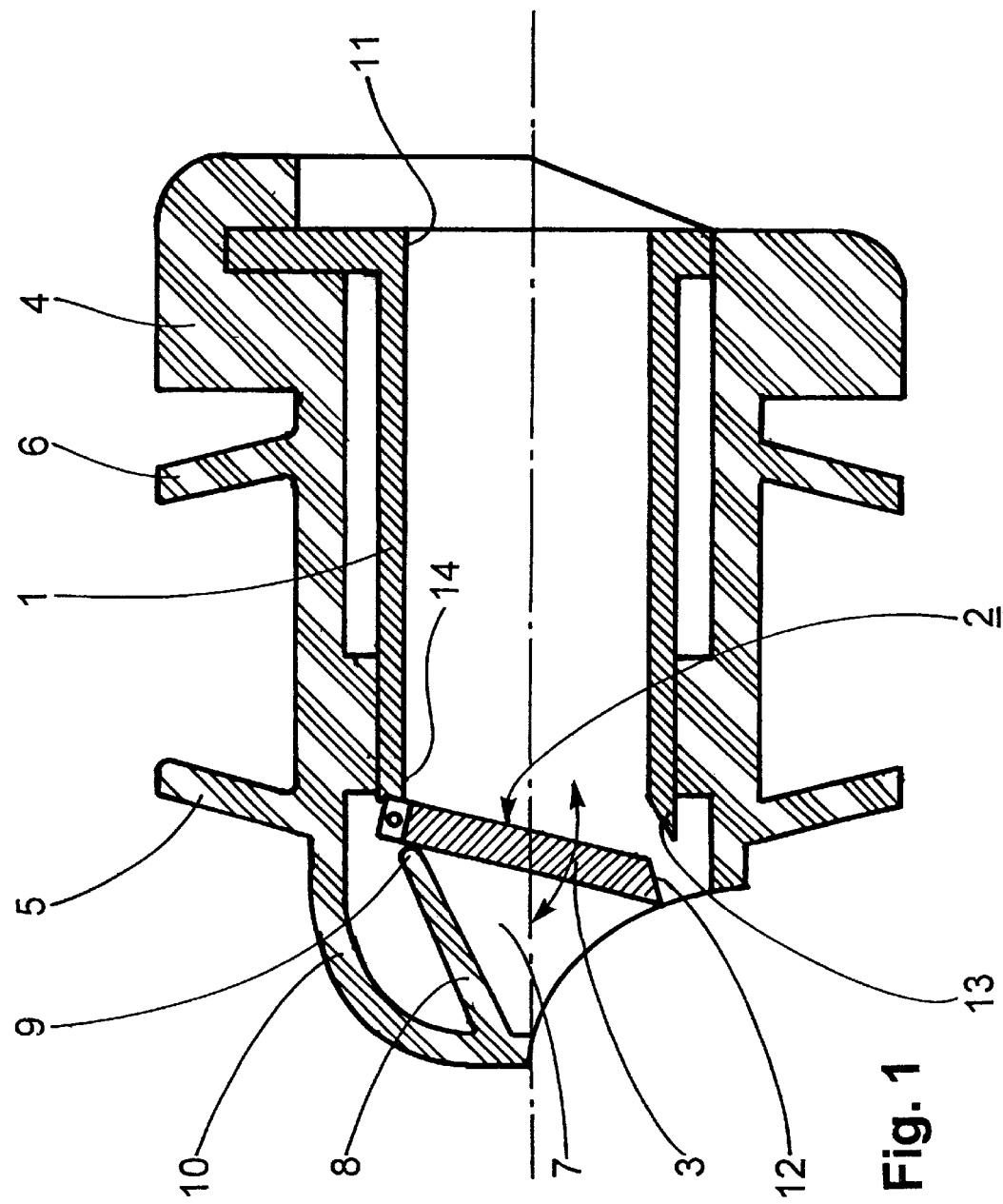

The tube-shaped part, which is inserted in the surgically produced connection channel between the trachea and the esophagus is indicated by reference number 1. On the end facing the trachea, the tube-shaped part 1 has an open lumen 11, which allows a sufficiently large air flow from the trachea into the esophagus. On the end facing the esophagus, a flap regulator valve 2 is arranged which, with its substantially truncated cone-shaped flap 3, can completely close the closable lumen end 14 of the tube-shaped part 1, when no air flow is active from the open lumen 11 to the valve flap, i.e. when no force acts to oppose the force that presses the flap 3 into the closed position. The tube-shaped part 1 is preferably inserted into the connection channel between the trachea and the esophagus in such a way that the flap 3 opens in the caudal direction, in order to thus certainly prevent a possible danger of the entrance of food particles or secretions into the lumen of the tube-shaped part 1. The opening and closing of the flap 3 in the closable lumen end 14 is indicated in the drawing by a double-headed arrow.

The truncated cone-shaped construction of the flap 3 is indicated by the chamfer 12, which finds its opposing piece in the chamfer 13 on the tube-shaped part 1, in order to obtain an optimal seal.

The tube-shaped part 1 is provided with a synthetic material (plastic) sheath 4, which is depicted here as an independent jacket part. On its periphery, the plastic material sheath 4 has two surrounding flanges 5 and 6, between which after insertion of the valve into the shunt, the esophagus wall and trachea wall are seated.

On the opposite end, i.e., on the esophagus side, the sheath 4 continues into a roof-like protuberance 10, which completely covers the pivot area of the flap 3 of the flap valve 2, and more or less forms a protective roof over the valve 2, in particular, when the shunt valve 1 is inserted, such that the protuberance 10 acts as a shield in the cranial direction.

The protuberance 10 does not function, however, only for shielding from food particles, etc. but also for mounting the restoring spring 8 on its rear (under) side. Here, the restoring spring 8 is depicted as a component that is constructed as a single piece with the sheath 4 and that impinges on the flap 3 of the valve 2 with a restoring or swing-back force. It has a length such that it rests with its free end 9 directly on the flap 3.

When the patient is conducting an air flow from the trachea into the esophagus, the flap 3 lifts up against the elastic spring force of the restoring spring 8, away from the tube-shaped part 1 and pivots into the pivot area 7. When the air flow lets up, or the air flow stops, the restoring spring 8 operates so that the flap 3 immediately seals off the open lumen of the tube-shaped part 1 again.

The sheath part 4 comprises, for the most part, silicone, the Shore hardness of which is adjustable, so that the restoring force from the restoring spring 8 on the pivoting of the flap 3 occurs in such a manner that it does not require any exertion at all to move the flap 3 away (off) the tube-shaped part 1 during inhalation.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

I claim:

1. A shunt valve for insertion into a surgically produced connecting channel between the trachea and the esophagus, comprising a tube-shaped part (1) having an open lumen end (11) to be turned toward the trachea when inserted and a closable lumen end (14) to be turned toward the esophagus when inserted, the closable lumen end (14) having a flap valve (2) acting on one side of the closable lumen end (14), the flap valve (2) comprising a flap (3) which stays in a closed position when there are no opposing forces, and which upon inhalation, in opening the flap (3), allows an air flow from the trachea into the esophagus, wherein the tube-shaped part (1) has a surrounding sheath (4) comprising a physiologically compatible plastic, wherein a pivot area (7) of the flap (3) of the flap valve (2) is substantially completely covered by a roof-like protuberance (10) of the plastic sheath (4), and wherein a restoring spring (8) is provided as a formation on the roof-like protuberance (10) of the plastic sheath (4), the restoring spring (8) having a free end (9) which contacts the flap (3) and generating an elastic force urging the flap (3) into the closed position.

2. The shunt valve according to claim 1, wherein the tube-shaped part (1) comprises a physiologically compatible metal.

3. The shunt valve according to claim 1, wherein two surrounding flanges (5, 6) protrude from an outer wall of the plastic sheath (4) to provide an area between the flanges (5,6) for receiving the esophagus wall and trachea.

4. The shunt valve according to claim 1, wherein the plastic sheath (4) comprises silicone.

* * * * *